(12) United States Patent
Sharma et al.

(10) Patent No.: US 10,298,252 B2
(45) Date of Patent: May 21, 2019

(54) DYNAMIC ANTI-ALIAS FILTER FOR ANALOG-TO-DIGITAL CONVERTER FRONT END

(71) Applicant: Analog Devices, Inc., Norwood, MA (US)

(72) Inventors: Yogesh Jayaraman Sharma, Santa Clara, CA (US); Arthur J. Kalb, Santa Clara, CA (US)

(73) Assignee: Analog Devices, Inc., Norwood, MA (US)

( * ) Notice: Subject to any disclaimer, the term of this patent is extended or adjusted under 35 U.S.C. 154(b) by 143 days.

(21) Appl. No.: 15/634,441

(22) Filed: Jun. 27, 2017

(65) Prior Publication Data

US 2018/0138920 A1 May 17, 2018

Related U.S. Application Data

(60) Provisional application No. 62/421,344, filed on Nov. 13, 2016, provisional application No. 62/421,650, filed on Nov. 14, 2016, provisional application No. 62/492,406, filed on May 1, 2017.

(51) Int. Cl.

| | |
|---|---|
| *H03M 1/12* | (2006.01) |
| *A61B 5/04* | (2006.01) |
| *A61B 5/0428* | (2006.01) |
| *H03M 1/06* | (2006.01) |

(Continued)

(52) U.S. Cl.
CPC ....... *H03M 1/1245* (2013.01); *A61B 5/04017* (2013.01); *A61B 5/04284* (2013.01); *A61B 5/04288* (2013.01); *H03M 1/0629* (2013.01); *H03M 1/00* (2013.01); *H03M 1/06* (2013.01); *H03M 1/10* (2013.01); *H03M 1/1009* (2013.01); *H03M 1/12* (2013.01)

(58) Field of Classification Search
CPC ............ H03M 1/12; H03M 1/00; H03M 1/10; H03M 1/1009; H03M 1/06
USPC ......................... 341/155, 158, 120, 122, 118
See application file for complete search history.

(56) References Cited

U.S. PATENT DOCUMENTS

| | | |
|---|---|---|
| 5,327,133 A | 7/1994 | Greene |
| 5,635,864 A | 6/1997 | Jones |
| 6,271,782 B1 | 8/2001 | Steensgaard-Madsen |

(Continued)

FOREIGN PATENT DOCUMENTS

DE    102010036793    4/2014

OTHER PUBLICATIONS

"U.S. Appl. No. 15/334,011, Notice of Allowance dated Oct. 17, 2017", 8 pgs.

(Continued)

*Primary Examiner* — Joseph J Lauture
(74) *Attorney, Agent, or Firm* — Schwegman Lundberg & Woessner, P.A.

(57) ABSTRACT

An analog front end system can include a filter bypass switch connected in a boot-strapped configuration to pull a control terminal of the filter bypass switch above or below a supply voltage. Using bootstrapped switches can allow both the charge injection and capacitive coupling of the bypass switches of a differential anti-alias filter (AAF) to be common mode. A differential input signal of the ADC is not affected by the charge injection and capacitive coupling of the bypass switches in the AAF filter to a first order.

20 Claims, 4 Drawing Sheets

(51) Int. Cl.
*H03M 1/10* (2006.01)
*H03M 1/00* (2006.01)

(56) References Cited

U.S. PATENT DOCUMENTS

| | | | |
|---|---|---|---|
| 7,095,345 | B2 | 8/2006 | Nguyen et al. |
| 7,385,443 | B1 | 6/2008 | Denison |
| 7,423,567 | B2 | 9/2008 | Melanson |
| 8,094,051 | B2 | 1/2012 | Bos |
| 8,265,769 | B2 | 9/2012 | Denison |
| 9,391,628 | B1 | 7/2016 | Lyden et al. |
| 9,419,642 | B1 | 8/2016 | Nguyen |
| 9,588,497 | B1 | 3/2017 | Monk et al. |
| 10,135,459 | B2 | 11/2018 | Sharma et al. |
| 2007/0126615 | A1 | 6/2007 | Km et al. |
| 2009/0079606 | A1 | 3/2009 | Terry et al. |
| 2009/0085785 | A1 | 4/2009 | Gerfers et al. |
| 2010/0066577 | A1 | 3/2010 | Huang |
| 2010/0075624 | A1 | 3/2010 | Shanan |
| 2012/0038500 | A1 | 2/2012 | Dijkmans et al. |
| 2012/0154193 | A1 | 6/2012 | Chang et al. |
| 2012/0281786 | A1 | 11/2012 | Lindemann et al. |
| 2015/0145571 | A1 | 5/2015 | Perrott |
| 2015/0256194 | A1 | 9/2015 | Saito |
| 2017/0230019 | A1* | 8/2017 | Chandrakumar .... A61B 5/7203 |
| 2018/0115320 | A1 | 4/2018 | Sharma et al. |
| 2018/0132750 | A1 | 5/2018 | Kalb et al. |

OTHER PUBLICATIONS

"U.S. Appl. No. 15/621,621, Preliminary Amendment filed Nov. 3, 2017", 6 pgs.
"U.S. Appl. No. 15/334,011, Examiner Interview Summary dated Apr. 16, 2018", 3 pgs.
"U.S. Appl. No. 15/334,011, Response filed May 21, 2018 to Non Final Office Action dated Feb. 21, 2018", 9 pgs.
"U.S. Appl. No. 15/334,011, Non Final Office Action dated Feb. 21, 2018", 4 pgs.
"German Application Serial No. 202017106869.2, German Search Report dated Aug. 9, 2018", 7 pgs.
"U.S. Appl. No. 15/334,011, Notice of Allowance dated Jul. 12, 2018", 7 pgs.
"U.S. Appl. No. 15/334,011, Response filed Aug. 9, 2017 to Non Final Office Action dated Feb. 10, 2017", 11 pgs.
"U.S. Appl. No. 15/334,011, Examiner Interview Summary dated Aug. 8, 2017", 3 pgs.
"U.S. Appl. No. 15/334,011, Non Final Office Action dated Feb. 10, 2017", 6 pgs.
"Optimum Selection of Capacitive Array for Multibit Sigma-Delta Modulators without DEM", (Jan. 1, 2009), 4 pgs.
Bohorquez, Jose L., et al., "A Digitally-Assisted Sensor Interface for Biomedical Applications", 2010 Symposium on VLSl Circuits / Technical Digest of Technical Papers, (2010), 217-218.
Bryant, Michael D., et al., "A Mixed Signal (Analog-Digital) Integrator Design", IEEE Transactions on Circuits and Systems-1: Regular Papers, 59)7), (Jul. 2012), 14-9.
Denison, Tim, et al., "A 2uW 100 n V/rtHz Chopper-Stabilized Instrumentation Amplifier for Chronic Measurement of Neutral Field Potentials", IEEE Journal of Solid-State Circuits, vol. 42, No. 12, (Dec. 2007), 2934-2945.
Muller, Rikky, et al., "A 0.13 mm2, 5uW, DC-Coupled Neutral Signal Acquisition IC With 0.5 V Supply", IEEE Journal of Solid-State Circuits, vol. 47, No. 1, (Jan. 2012), 232-243.
U.S. Appl. No. 15/334,011, filed Oct. 25, 2016, ADC With Capacitive Difference Circuit and Digital Sigma-Delta Feedback.
U.S. Appl. No. 15/621,621, filed Jun. 13, 2017, Quantization Noise Cancellation in a Feedback Loop.
"U.S. Appl. No. 15/334,011, Preliminary Amendment Filed, Jan. 11, 2018", 8 pgs.

* cited by examiner

DYNAMIC ANTI-ALIAS FILTER FOR ANALOG-TO-DIGITAL CONVERTER FRONT END

CLAIM OF PRIORITY

This application claims the benefit of priority of U.S. Provisional Patent Application Ser. No. 62/421,344, titled "INTERFERENCE-IMMUNE DIAGNOSTIC QUALITY ECG RECORDING FOR WIRELESS PATIENT MONITORING APPLICATIONS" to Arthur J. Kalb et al., filed on Nov. 13, 2016, and U.S. Provisional Patent Application Ser. No. 62/421,650, titled "INTERFERENCE-IMMUNE DIAGNOSTIC QUALITY ECG RECORDING FOR WIRELESS PATIENT MONITORING APPLICATIONS" to Arthur J. Kalb et al., filed on Nov. 14, 2016, and U.S. Provisional Patent Application Ser. No. 62/492,406, titled "QUANTIZATION NOISE CANCELLATION IN A FEEDBACK LOOP" to Arthur J. Kalb et al., filed on May 1, 2017, the entire contents of each being incorporated herein by reference.

FIELD OF THE DISCLOSURE

This disclosure relates generally to integrated circuits, and more particularly but not by way of limitation, to low noise precision input stages for analog-to-digital converters.

BACKGROUND

In many electronics applications, an analog-to-digital converter (ADC) can translate analog electrical signals representing real-world phenomenon, e.g., light, sound, temperature, or pressure, to a digital output signal using for digital processing, e.g., for further signal processing. For instance, in precision measurement systems, electronics can be provided with one or more sensors to make measurements and generate analog signals. The analog signals can be provided to an ADC to generate a digital output signal for further processing.

ADCs can be found in many places such as broadband communication systems, audio systems, receiver systems, etc. ADCs can be used in a broad range of applications including communications, energy, healthcare, instrumentation and measurement, motor and power control, industrial automation and aerospace/defense.

SUMMARY OF THE DISCLOSURE

Analog-to-digital converters (ADCs) can be used for various applications, including in wireless patient monitoring applications, for example. The present inventors have recognized that one problem to be solved is aliasing due to sampling of out of band noise or interference. The present inventors have recognized that a dynamic anti-alias filter (AAF) coupled before an ADC circuit can include a bypass switch that can inject significant charge into the AAF filter capacitor due to charge injection and capacitive coupling when the bypass switch turns off, which can cause differential error at the ADC input. The present inventors have solved this problem by recognizing that a boot-strapped bypass switch can be incorporated into the dynamic AAF filter, which can make charge injection and capacitive coupling independent of input signal. As a result, the settling time requirements can be relaxed considerably, which can provide a better trade-off between noise aliasing and power consumption/bandwidth of the amplifier driving the AAF filter and the ADC.

In some aspects, this disclosure is directed to an analog front end (AFE) system including an anti-alias filter circuit having a filter bypass switch configured to provide at least one of a charge injection and a clock feedthrough that is independent of an input signal. The AFE system comprising at least one sampling capacitor of an analog-to-digital converter (ADC) circuit configured to sample an output of the anti-alias filter circuit, a gain or buffer circuit including an input to receive the input signal, and the anti-alias filter circuit coupled to an output of the gain or buffer circuit, the filter circuit including: a filter resistor; a filter capacitor coupled to a terminal of the filter resistor; and the filter bypass switch connected in a boot-strapped configuration to pull a control terminal of the filter bypass switch above or below a supply voltage, the filter bypass switch connected in parallel with the filter resistor, the filter bypass switch including an ON state and an OFF state, wherein when in the ON state, the filter bypass switch is configured to bypass the filter resistor allowing the gain or buffer circuit to drive the at least one sampling capacitor through the filter bypass switch; and wherein when in the OFF state, the filter bypass switch is configured to cause the gain or buffer circuit to drive the at least one sampling capacitor through the filter resistor.

In some aspects, this disclosure is directed to a method of operating an analog front end (AFE) system including an anti-alias filter circuit having a filter bypass switch configured to provide at least one of a charge injection and a clock feedthrough that is independent of an input signal. The method comprises providing at least one sampling capacitor of an analog-to-digital converter (ADC) circuit configured to sample the output of the anti-alias filter circuit, providing a gain or buffer circuit including an input to receive the input signal, and coupling the anti-alias filter circuit to the output of the gain or buffer circuit, the anti-alias filter circuit including a filter resistor, a filter capacitor coupled to a terminal of the filter resistor, and the filter bypass switch connected in a boot-strapped configuration to pull a control terminal of the filter bypass switch above or below a supply voltage, the filter bypass switch connected in parallel with the filter resistor, the filter bypass switch including an ON state and an OFF state, wherein when in the ON state, receiving the input signal and controlling the filter bypass switch to bypass the filter resistor to allow the gain or buffer circuit to drive the at least one sampling capacitor through the filter bypass switch, and wherein when in the OFF state, receiving the input signal and controlling the filter bypass switch to cause the gain or buffer circuit to drive the at least one sampling capacitor through the filter resistor.

In some aspects, this disclosure is directed to an electrocardiogram (ECG) measurement circuit comprising: an analog front end (AFE) system including an anti-alias filter circuit having a filter bypass switch configured to provide at least one of a charge injection and a clock feedthrough that is independent of an input signal. The AFE system comprises at least one sampling capacitor of an analog-to-digital converter (ADC) circuit configured to sample the output of the anti-alias filter circuit; a gain or buffer circuit including an input to receive the input signal; and the anti-alias filter circuit coupled to the output of the gain or buffer circuit, the filter circuit including: a filter resistor; a filter capacitor coupled to a terminal of the filter resistor; and the filter bypass switch connected in a boot-strapped configuration to pull a control terminal of the filter bypass switch above or below a supply voltage, the filter bypass switch connected in parallel with the filter resistor, the filter bypass switch including an ON state and an OFF state, wherein when in the ON state, the filter bypass switch is configured to bypass the filter resistor allowing the gain or buffer circuit to drive the at least one sampling capacitor through the filter bypass switch; and wherein when in the OFF state, the filter bypass switch is configured to cause the gain or buffer circuit to drive the at least one sampling capacitor through the filter resistor.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

Figure 1:
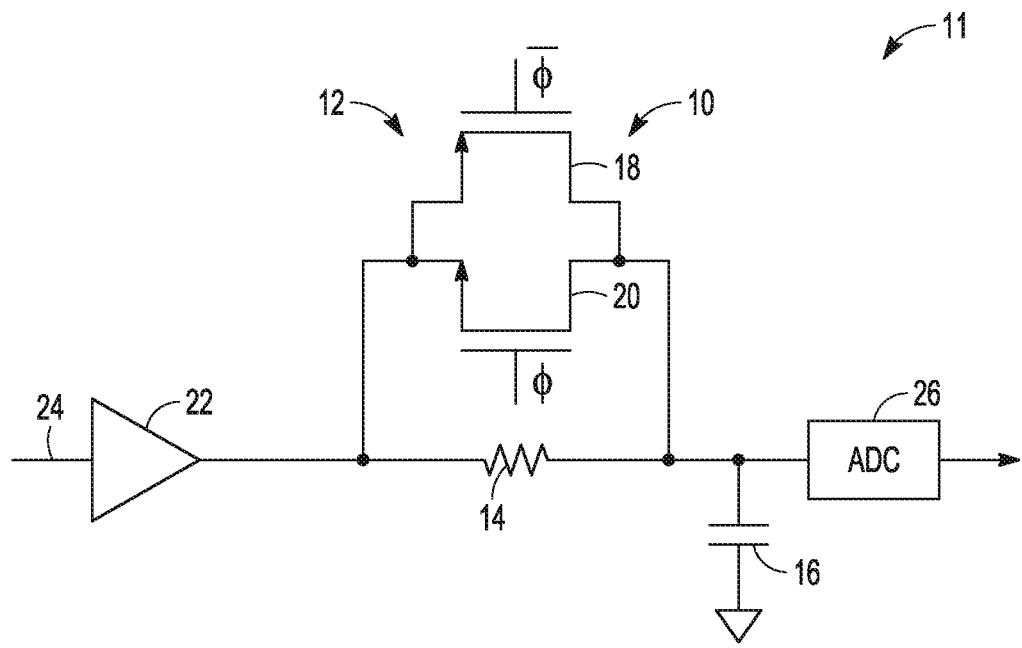
FIG. 1 depicts an example of a dynamic anti-alias filter circuit.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Anti-alias filter circuits (AAF) can be used before an analog-to-digital converter (ADC) input stage (or front end) to prevent aliasing (due to sampling) of out of band noise/interference into in-band signal range by filtering the out of band frequency content. The AAF can be a low pass filter circuit, a band pass filter circuit, a high pass filter circuit, etc. An amplifier can be used to amplify the input signal and drive the ADC front end through the AAF filter. The AAF filter bandwidth can be a trade-off between settling time desired to meet precision requirements and rejection of out-of-band noise/interference.

Dynamic AAF filters can be used to overcome this limitation, as described in commonly assigned U.S. Pat. No. 9,391,628, titled "Low noise precision input stage analog-to-digital converters," to Colin Lyden et al. A dynamic AAF filter can include a bypass switch that can be used to bypass the AAF filter so that the amplifier can drive an ADC sampling capacitor directly for a short period of time to achieve a fast settling duration. Later, the bypass switch can be turned off and the amplifier can drive the ADC sampling capacitor through the AAF filter during the final settling duration. During this period, the AAF filter can attenuate out of band noise/interference before the ADC samples the input signal.

A challenge with dynamic AAF filters, e.g., in an analog front end (AFE), can be that the bypass switch can inject significant charge into the AAF filter capacitor due to charge injection and capacitive coupling when the bypass switch turns off, which can cause error. These errors can be a function of the input voltage and can cause differential signal error. This differential error should be "settled" by the time the input sampling capacitor of the ADC goes to the hold state. Thus, a significant amount of sampling period can be spent in this mode to meet the precision settling requirements, which can reduce the time available for the amplifier direct settling. This can lead to greater power consumption in the amplifier for wider amplifier bandwidth to get faster settling.

As described in detail below, the present inventors have recognized that a filter bypass switch connected in a boot-strapped configuration to pull a control terminal of the filter bypass switch above or below a supply voltage can be used to solve the problems mentioned above. Using bootstrapped switches can allow both the charge injection and capacitive coupling of the bypass switches of the differential AAF filter to be common mode. The boot strapped switch can be a single type of transistor, e.g., one of an N-type FET or a P-type FET, where the gate can be driven to the input voltage when the switch is off but driven to the input voltage plus supply voltage when the switch is on. Thus, to a first order, the differential input signal of the ADC is not affected by the charge injection and capacitive coupling of the bypass switches in the AAF filter. In some implementations, only 30% of the sampling period was used when the AAF filter was active, which greatly reduced power consumption of the amplifier.

FIG. 1 depicts an example of a dynamic anti-alias filter circuit 10. The dynamic AAF circuit 10, which can form a part of an analog front end (AFE) system 11, can include a filter bypass switch 12, a filter resistor 14, and a filter capacitor 16 coupled to a terminal of the filter resistor 14. The filter bypass switch 12 can be, for example, a transmission gate including a first transistor 18 and a second transistor 20. In some examples, the first and second transistors 18, 20 can be field-effect transistors where the first transistor 18 is a first type, e.g., P-type, and the second transistor 20 is a second type, e.g., N-type. As seen in FIG. 1, the first and second transistors 18, 20 can be controlled using complimentary control signals φ and φ_bar such that both transistors 18, 20 are either ON or OFF over a wider range of voltages than either would be individually.

The AFE system 11 can further include a gain circuit 22, e.g., a capacitive gain amplifier (CGA) having an input to receive an input signal 24 and an output configured to apply a signal to the filter bypass switch 12. For example, the gain circuit 22 can provide an input to the dynamic anti-alias filter circuit 10, and the dynamic anti-alias filter circuit 10 can output a filtered signal to an analog-to-digital converter (ADC) circuit 26 for conversion to a digital signal. For example, at least one sampling capacitor of an analog-to-digital converter (ADC) circuit can sample an output of the anti-alias filter circuit. In some examples, the gain circuit 22 can be a buffer circuit.

In some examples, the filter capacitor 16 can include an ADC sampling capacitor of the ADC circuit 26. The bypass switch 12 can be used to bypass the AAF filter circuit so that the gain circuit 22 can drive an ADC sampling capacitor directly for a short period of time. Later, the bypass switch 12 can be turned OFF and the gain circuit 22 can drive the ADC sampling capacitor through the AAF filter circuit during the final settling duration. The AAF filter can attenuate out of band noise/interference before the ADC samples the input signal.

In FIG. 1, when the filter bypass switch 12 is turned ON, the gain circuit 22 can drive the filter capacitor 16, e.g., an ADC sampling capacitor, by bypassing the filter resistor 14. Then, the filter bypass switch 12 can be turned OFF, which connects the filter resistor 14 to the gain circuit 22, and input signal from the gain circuit 22 can be provided to the ADC through the RC filter that includes the filter resistor 14 and the filter capacitor 16.

When the filter bypass switch 12 is ON and the input is below Vdd/2, the second transistor 20, e.g., N-type device, can be active but the first transistor 18, e.g., P-type device, can be OFF. When the filter bypass switch 12 is turned OFF, two sources of error can occur: charge injection and clock feed through. Charge injection can cause errors due to the channel charge being dispersed into the drain and source terminals of the transistor when the transistor turns off. Clock feed through can cause errors due to the control signal φ and φ_bar, e.g., a clock signal, coupling into the circuit via the gate-drain or gate-source overlap capacitance, for example.

When the switch turns OFF, the channel charge injection through the second transistor 20 can split to both the source and drain but because the input impedance on the filter capacitor 16 is lower than the input impedance of the amplifier 22, most of the gate charge goes to the filter capacitor 16. Similar behavior can occur when the input is above Vdd/2 when the first transistor 18 is ON but the second transistor 20 is OFF. Thus the input voltage to the ADC can be corrupted by the charge injection of the bypass switch that changes with the input voltage of the AAF Filter.

Charge injection at the bypass switch can be described by Equations 1 and 2 below:

$$Q_{chn} \cong -W_n L_n C_{ox} (\phi_H - V_{IN} - V_{tn})$$ Equation 1:

$$Q_{chp} \cong W_p L_p C_{ox} (V_{IN} - \phi_L - |V_{tp}|)$$ Equation 2:

Equation 1 describes the N-channel charge injection and Equation 2 describes the P-channel charge injection. In Equations 1 and 2, $\phi_H$ (e.g., 5 Volts (V)) and $\phi_L$ (e.g., 0 V) are the high and low levels of the filter bypass switch 12, $V_{IN}$ is the input voltage (e.g., 0-5 V), $V_{tn}$ is the N-channel threshold voltage, $V_{tp}$ is the P-channel threshold voltage, W and L are width and length of the transistor, and $C_{ox}$ is the oxide capacitance of the transistor.

In Equation 1, the N-channel charge injection is a function of the difference between $\phi_H$ and $V_{IN}$. As voltage $V_{IN}$ increases and approaches $\phi_H$, the N-channel charge injection decreases. The P-channel charge injection is a function of the difference between $V_{IN}$ and $\phi_L$. As voltage $V_{IN}$ increases, the P-channel charge injection increases.

At an input voltage $V_{IN}$ near a mid-range, the N-channel and P-channel charge injections can cancel each other. However, as the input voltage $V_{IN}$ approaches the high or low side of a range, the N-channel and P-channel charge injections may not cancel each other.

Although drawn single ended, the circuit in FIG. 1 can also be connected in a differential configuration. A differential configuration can result in a significant voltage kick at the output (e.g., 2 mV), when, for input voltage $V_{IN}$ approach the high or low side of a range, the P-channel device can inject charge into the filter capacitor 16 while the N-channel device is off or vice versa. This voltage kick can be settled by the RC filter of the filter resistor 14 and the filter capacitor 16, but it can require a significant of settling time.

As mentioned above, when the filter bypass switch 12 is turned OFF, clock feed through can be another source of error. Clock feed through can be described by Equation 3 below:

$$V_{out} = V_{in} - \frac{C_{ol}}{C_{ol} + C} (\phi_H - \phi_L)$$ Equation 3

In Equation 3, $\phi_H$ and $\phi_L$ are the high and low levels of the control signal, e.g., the clock signal, of the filter bypass switch 12, $C_{ol}$ is the overlap capacitance of the transistor, and C is the capacitance of the output capacitor, e.g., the filter/sampling capacitor 16. If the difference between $\phi_H$ and $\phi_L$ is a fixed value, the $V_{OUT}$ voltage kick caused is the same regardless of input. As such, the output clock feed through is not signal dependent. But, if $\phi_H$ or $\phi_L$ is a function of the input voltage, then the $V_{OUT}$ voltage kick caused is a function of the input voltage.

In some implementations, for the purpose of illustration only, a 4/1 CMOS switch with an 8 pF filter capacitor can cause a 3 mV output error due to charge injection for an input differential voltage of 1.2V. However, it can be desirable to achieve the input of the ADC to settle to less than 5 uV. As such, an RC time constant (tau) of 6.4 was needed. For a 240 kilohertz (kHz) AAF filter circuit, tau is 660 nanoseconds (ns). However, 6.4 tau equals 4.2 us, which leaves no time for the gain circuit 22, e.g., CGA, to settle if the ADC is sampling at 240 kHz.

As indicated above, the present inventors have solved this problem by recognizing that a boot-strapped bypass switch can be incorporated into the dynamic AAF filter, which can make charge injection and capacitive coupling independent of input signal. Thus, the charge injection and capacitive coupling will be common-mode and can be rejected.

Figure 2:
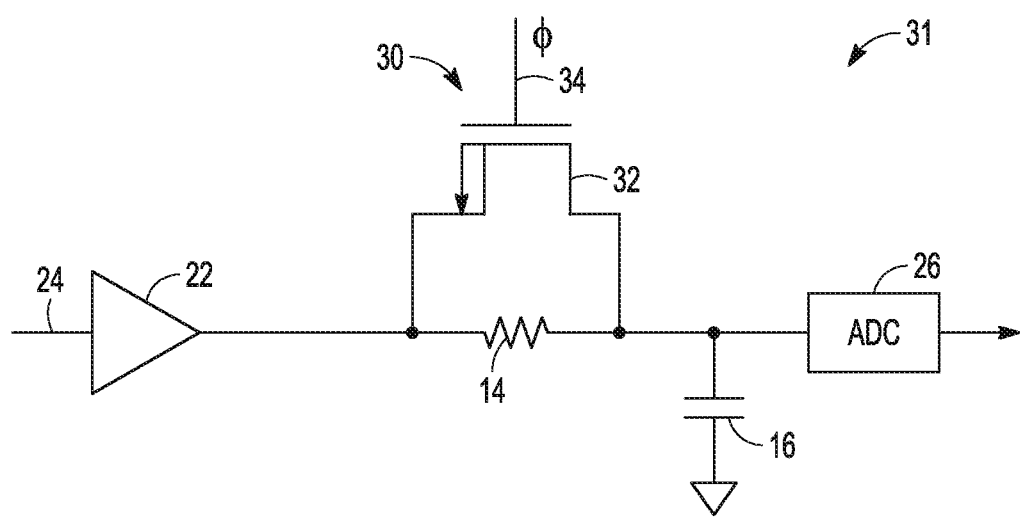
FIG. 2 depicts an example of a dynamic anti-alias filter circuit that can implement various techniques of this disclosure.
Figure 3:
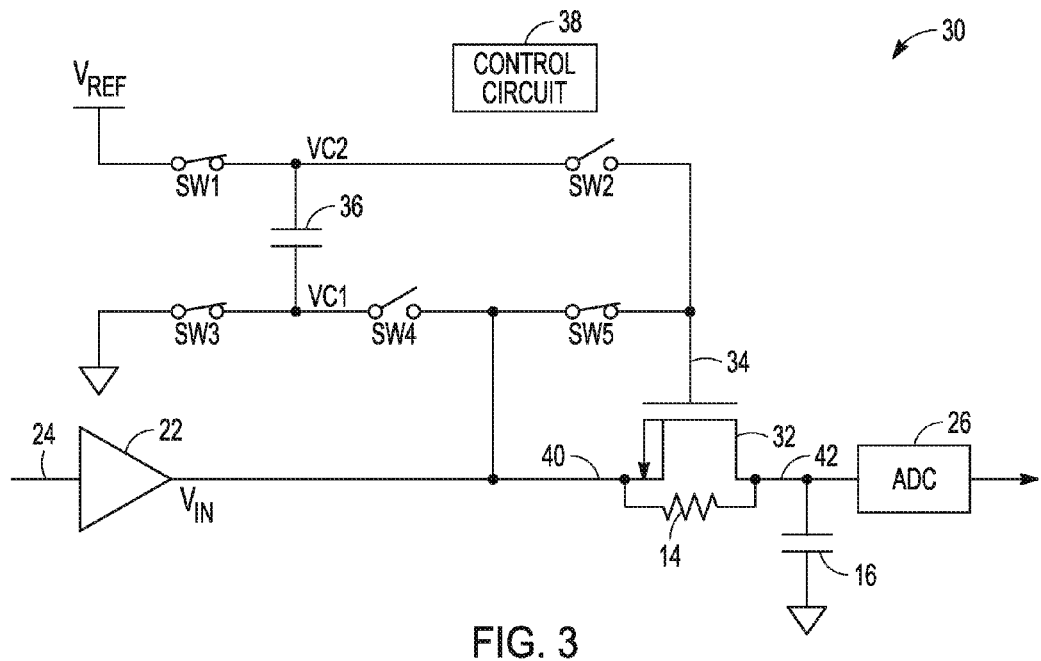
FIG. 3 depicts an example of a dynamic anti-alias filter circuit including a filter bypass switch connected in a boot-strapped configuration.
Figure 4:
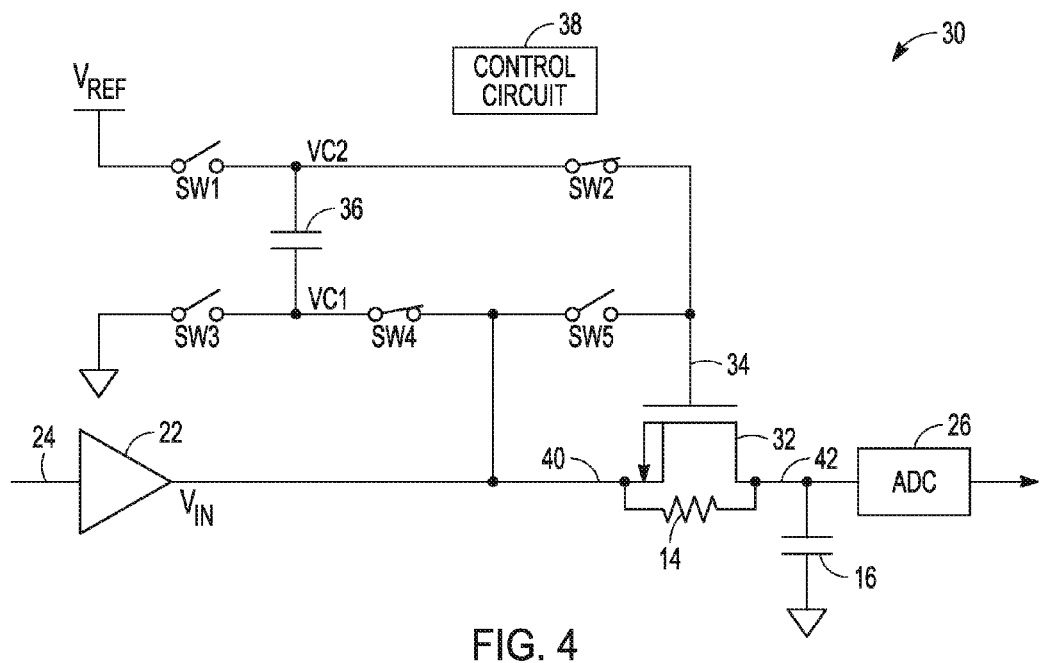
FIG. 4 depicts the example of a dynamic anti-alias filter circuit of FIG. 3 including the filter bypass switch in an ON state.

FIG. 2 depicts an example of a dynamic anti-alias filter circuit 30 that can implement various techniques of this disclosure. The dynamic AAF circuit 30, which can form a part of an analog front end (AFE) system 31, can include a filter bypass switch 32 (connected in a boot-strapped configuration as shown in FIGS. 3 and 4), a filter resistor 14, and a filter capacitor 16 coupled to a terminal of the filter resistor 14. The filter circuit 30 can be coupled to the output of the gain or buffer circuit 22.

In some examples, the filter capacitor 16 and an ADC sampling capacitor of the ADC circuit 26 are the same capacitor and, in other examples, the filter capacitor 16 and an ADC sampling capacitor can be different capacitors.

In some example configurations, the filter bypass switch 32 can be a single transistor, as shown in FIG. 2. In some examples, the filter bypass switch 32 can be a single type of transistor and only one of an N-type transistor and a P-type transistor. The transistor can be, for example, a field-effect transistor (FET) including, but not limited to, a metal-oxide semiconductor field-effect transistor (MOSFET) and a junction gate field-effect transistor (JFET), a DMOS transistor, and a gallium nitride transistor.

As seen in FIG. 2, the filter bypass switch 32 can be controlled by applying a control signal $\phi$ at a control terminal 34 to turn the switch 32 ON or OFF. For example, the control terminal can be a gate terminal of a FET. A gain circuit 22, e.g., a capacitive gain amplifier (CGA), can provide an input to the dynamic anti-alias filter circuit 30, and the dynamic anti-alias filter circuit 30 can output a filtered signal to an analog-to-digital converter (ADC) circuit 26 for conversion to a digital signal.

FIG. 3 depicts an example of a dynamic anti-alias filter circuit including a filter bypass switch connected in a boot-strapped configuration. In particular, the filter circuit 30 depicts the filter bypass switch 32 in an OFF state. When in the OFF state, the filter bypass switch 32 can cause the gain circuit 22 or buffer circuit to drive the filter capacitor 16, e.g., one or more sampling capacitors, through the filter resistor 14.

In the example configuration shown, the anti-alias filter circuit 30 can include a number of boot-strap switches, shown as switches SW1-SW5, to pull a control terminal of the filter bypass switch 32, e.g., a gate terminal of a transistor, above or below a supply voltage to turn the switch ON or OFF. In addition, the filter circuit 30 can include one or more boot-strap capacitors 36. A control circuit 38 of an ADC system having control lines (not depicted) coupled to the switches SW1-SW5 can control operation of the switches SW1-SW5.

As seen in FIG. 3, the control circuit 38 can close the switch SW5 to couple the control terminal 34 of the filter bypass switch 32, e.g., a gate terminal of a FET, to the output of the gain circuit 22, which can turn OFF the filter bypass switch 32. The control circuit 38 can open the switches SW2 and SW3 to decouple the boot-strap capacitor(s) 36 from 1) the control terminal 34 of the bypass switch 32 and 2) an input terminal 40, e.g., source terminal, of the bypass switch 32. When the control circuit 38 closes the switches SW1 and SW3, the boot-strap capacitor(s) 36 can then charge up to the supply voltage $V_{REF}$, e.g., 5V.

FIG. 4 depicts the example of a dynamic anti-alias filter circuit of FIG. 3 including the filter bypass switch in an ON state. When in the ON state, the filter bypass switch 32 can bypass the filter resistor 14 and allow the gain circuit 22 to drive the filter capacitor 16, e.g., one or more sampling capacitors, via the source terminal 40 and the drain terminal 42 of the bypass switch 32.

As seen in FIG. 4, the control circuit 38 can open the switches SW1 and SW3 to decouple the boot-strap capacitor(s) 36 from the supply voltage $V_{REF}$. The control circuit 38 can open the switch SW5 and close switches SW2, SW4 to couple the boot-strap capacitor(s) to 1) the control terminal 34 of the bypass switch 32 and 2) the input terminal 40 of the bypass switch 32 to apply a combination, e.g., sum or difference, of the supply voltage $V_{REF}$ and a voltage of the input signal 24 $V_{IN}$ at the control terminal 34 of the bypass switch 32. The control terminal 34 of the bypass switch 32 is at a voltage $V_{REF}+V_{IN}$ and the input terminal 40 of the bypass switch 32 is at a voltage $V_{IN}$, resulting in a voltage of $V_{REF}$ between the control terminal 34 and the input terminal 40, e.g., a gate-source voltage of $V_{REF}$, which can turn the bypass switch 32 ON. Note that the gate-source voltage of the bypass switch 32 is independent of the input voltage 24.

Referring again to the charge injection issue described above, if the bypass switch 32 is a P-type device, the charge injection is a function of the input voltage $V_{IN}$ minus the low level $\phi_L$ of the bypass switch 32. Using the boot-strapping techniques of FIGS. 3 and 4, the low level voltage $\phi_L$ is the input voltage $V_{IN}$, so the charge injection of the bypass switch becomes independent of the input voltage.

If the bypass switch 32 is an N-type device, the charge injection is a function of the high level voltage $\phi_H$ of the bypass switch 32 minus the input voltage $V_{IN}$. Using the boot-strapping techniques of FIGS. 3 and 4, the high level voltage $\phi_H$ is the input voltage $V_{IN}$ plus $V_{REF}$, so the high level voltage $\phi_H$ ($V_{IN}+V_{REF}$) minus the input voltage $V_{IN}$ equals $V_{REF}$. In this manner, the charge injection is made independent of the input signal.

Referring again to the clock feed through issue described above, clock feed through is a function of the difference between high and low levels $\phi_H$ and $\phi_L$ of the filter bypass switch 32. Using the boot-strapping techniques of FIGS. 3 and 4, the high level voltage $\phi_H$ is the input voltage $V_{IN}$ plus $V_{REF}$ and the low level voltage $\phi_L$ is the input voltage $V_{IN}$. So the high level voltage $\phi_H$ ($V_{IN}+V_{REF}$) minus the low level voltage $\phi_L$ ($V_{IN}$) equals $V_{REF}$. In this manner, the clock feed through is made independent of the input signal.

Figure 5:
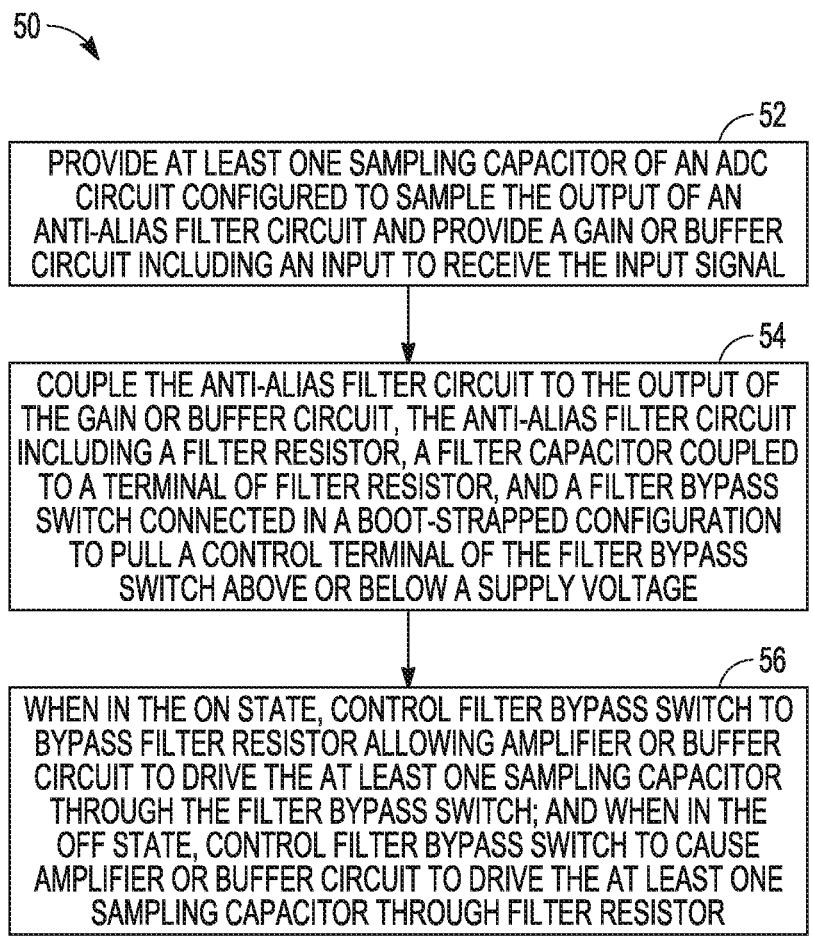
FIG. 5 is a flow diagram representing an example of a method of operating an analog front end (AFE) system including an anti-alias filter circuit having a filter bypass switch configured to provide at least one of a charge injection and a clock feedthrough that is independent of an input signal, using various techniques of this disclosure.

FIG. 5 is a flow diagram representing an example of a method 50 of operating an analog front end (AFE) system including an anti-alias filter circuit having a filter bypass switch configured to provide at least one of a charge injection and a clock feedthrough that is independent of an input signal, using various techniques of this disclosure. At block 52, the method 50 can include providing one or more sampling capacitors of an ADC circuit configured to sample the output of the anti-alias filter circuit. For example, the analog front end system 31 of FIG. 2 can include an ADC circuit having one or more sampling capacitors, e.g., capacitor 16, configured to sample the output of the anti-alias filter circuit 30.

At block 54, the method 50 can include providing a gain or buffer circuit including an input to receive the input signal. For example, the analog front end system 31 of FIG. 2 can include a gain or buffer circuit 22 to receive an input signal 24.

At block 56, the method 50 can include providing a filter circuit coupled to the output of the gain or buffer circuit, including providing a filter resistor, providing a filter capacitor coupled to a terminal of the filter resistor, and providing a filter bypass switch connected in a boot-strapped configuration to pull a control terminal of the filter bypass switch above or below a supply voltage, the filter bypass switch connected in parallel with the filter resistor, the filter bypass switch including an ON state and an OFF state. For example, the AFE system of FIGS. 2-4 can include a filter circuit 30 including filter resistor 14, filter capacitor 16, and a filter bypass switch 32 connected in a boot-strapped configuration.

At block 56, the method 50 can include, when in the ON state, controlling the filter bypass switch to bypass the filter resistor allowing the gain or buffer circuit to drive the sampling capacitor(s), and when in the OFF state, controlling the filter bypass switch to cause the gain or buffer circuit to drive the sampling capacitor(s) through the filter resistor. For example, as seen in FIG. 4, the control circuit 38 can control the filter bypass switch 32 to turn ON and bypass the filter resistor 14 allowing the gain or buffer circuit 22 to drive the sampling capacitor(s), e.g., capacitor 16. As seen in FIG. 3, the control circuit 38 can control the filter bypass switch 32 to turn OFF and to cause the gain or buffer circuit 22 to drive the sampling capacitor(s), e.g., capacitor 16, through the filter resistor 14.

Figure 6:
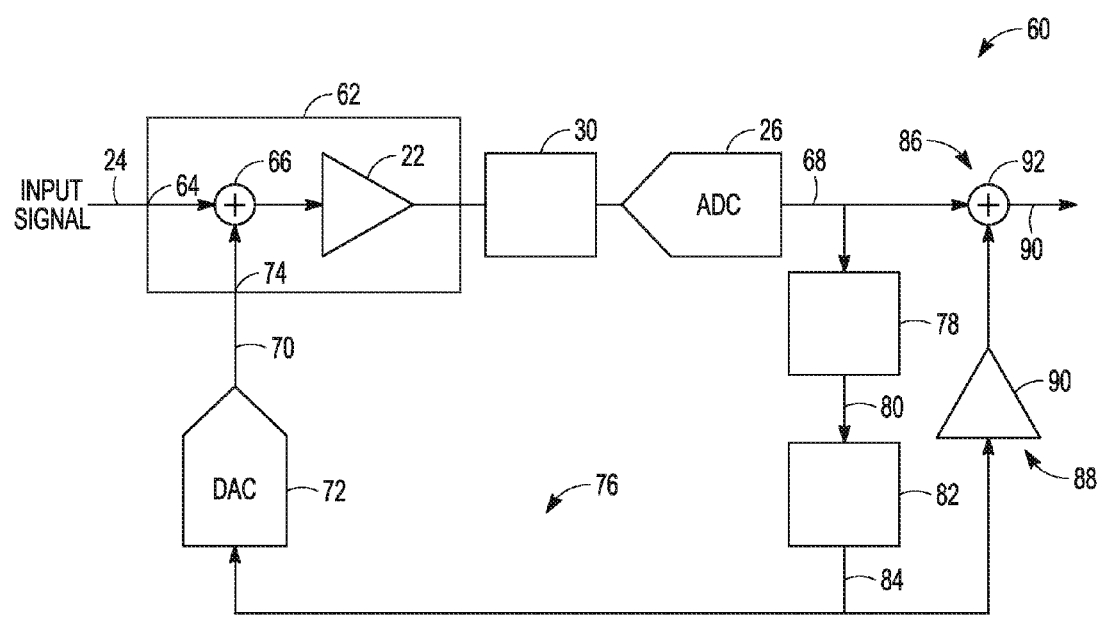
FIG. 6 an example of a schematic diagram of the analog front end system of FIGS. 2-4 in combination with an electrocardiogram (ECG) measurement circuit.

FIG. 6 an example of a schematic diagram of the analog front end system 31 of FIGS. 2-4 in combination with an electrocardiogram (ECG) measurement circuit 60. The system 60 can include a gain circuit 62 having a first input 64 to receive an analog input signal 24, the dynamic anti-alias filter circuit 30 (including a filter bypass switch), and an ADC circuit 26, e.g. a sigma-delta ADC or successive approximation register (SAR) ADC, to receive an output of the AAF filter circuit 30. In the example configuration shown, the gain circuit 62 can include an adder circuit 66 and a gain or buffer circuit 22, e.g. a capacitive gain amplifier (CGA).

The ADC 26 can generate a first digital output signal 68 corresponding to the analog input signal 24, e.g. an ECG output signal. As seen in FIG. 6, the analog signal 70 from a digital-to-analog converter (DAC) circuit 72 can be applied to a second input 74 of the gain circuit 62. The adder circuit 66 can subtract the analog output signal 70 from the DAC circuit 72 from the original analog input signal 24. It should be noted that the adder circuit 66 is depicted for conceptual purposes but in some configurations can form a part of the gain or buffer circuit 22 itself. In some examples, the subtraction and gain can be performed in a CGA, which can then be fed into a high resolution ADC 26, such as a sigma-delta converter, for linearity.

A feedback loop 76 of FIG. 6 can include a frequency-selective filter circuit 78 to receive the digital output signal 68 of the ADC circuit 26 and provide an output signal 80 to a quantizer circuit 82, e.g. a digital sigma-delta modulator. In some example implementations, the frequency-selective filter circuit 78 can include one or both of an integrator circuit and a low-pass filter circuit.

As seen in FIG. 6, the quantizer circuit 82 can output a quantized signal 84 to the DAC 72. In some examples implementations, the DAC 72 can be a noise-shaped DAC circuit, e.g. a sigma-delta DAC. In some examples, the filter circuit output signal 80 can include a first number of bits, e.g. 16 bits, and the quantized signal 84 can include a second number of bits less than the first number of bits, e.g. 7 bits.

An AFE system output circuit 86 a recombination path 88 including, for example, a scaling circuit 90 and an adder circuit 92. The adder circuit 92 can combine a scaled version of the quantized signal 84 with the digital output signal 68 from the ADC 26 to generate an output signal 90, e.g. an ECG output signal. Along with reconstructing the input signal 24, this recombination can substantially eliminate the quantizer circuit 82 quantization noise. Additional information regarding the recombination path 88 can be found in commonly assigned U.S. patent application Ser. No. 15/621,621, titled "QUANTIZATION NOISE CANCELLATION IN A FEEDBACK LOOP," to Kalb et al. and filed on Jun. 13, 2017, the entire contents of which being incorporated herein by reference.

VARIOUS NOTES

Each of the non-limiting aspects or examples described herein may stand on its own, or may be combined in various permutations or combinations with one or more of the other examples.

The above detailed description includes references to the accompanying drawings, which form a part of the detailed description. The drawings show, by way of illustration, specific embodiments in which the invention may be practiced. These embodiments are also referred to herein as "aspects" or "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact discs and digital video discs), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. An analog front end (AFE) system including an anti-alias filter circuit having a filter bypass switch configured to provide at least one of a charge injection and a clock feedthrough that is independent of an input signal, the AFE system comprising:
at least one sampling capacitor of an analog-to-digital converter (ADC) circuit configured to sample an output of the anti-alias filter circuit;
a gain or buffer circuit including an input to receive the input signal; and
the anti-alias filter circuit coupled to an output of the gain or buffer circuit, the filter circuit including:
a filter resistor;
a filter capacitor coupled to a terminal of the filter resistor; and
the filter bypass switch connected in a boot-strapped configuration to pull a control terminal of the filter bypass switch above or below a supply voltage, the filter bypass switch connected in parallel with the filter resistor, the filter bypass switch including an ON state and an OFF state,
wherein when in the ON state, the filter bypass switch is configured to bypass the filter resistor allowing the gain or buffer circuit to drive the at least one sampling capacitor through the filter bypass switch; and
wherein when in the OFF state, the filter bypass switch is configured to cause the gain or buffer circuit to drive the at least one sampling capacitor through the filter resistor.

2. The AFE system of claim 1, wherein the filter bypass switch connected in a boot-strapped configuration includes:
the bypass switch having an input terminal configured to receive the input signal, an output terminal, and the control terminal, and;
at least one boot-strap capacitor; and
a plurality of boot-strap switches configured to:
when the filter bypass switch is in the OFF state, couple the at least one boot-strap capacitor to a supply voltage to charge the at least one boot-strap capacitor to the supply voltage, couple the control terminal of the bypass switch to the input terminal of the bypass switch, and decouple the at least one boot-strap capacitor from 1) the control terminal of the bypass switch and 2) the input terminal of the bypass switch, and
when the filter bypass switch is in the ON state, decouple the at least one boot-strap capacitor from the supply voltage, and couple the at least one boot-strap capacitor to 1) the control terminal of the bypass switch and 2) the input terminal of the bypass switch to apply a combination of the supply voltage and a voltage of the input signal at the control terminal of the bypass switch.

3. The AFE system of claim 2, further comprising:
a control circuit configured to manage switch configurations of the plurality of boot-strap switches.

4. The AFE system of claim 1, wherein the bypass switch is a single transistor.

5. The AFE system of claim 1, wherein the bypass switch is a single type of field-effect transistor (FET) being only one of an N-type FET or a P-type FET.

6. The AFE system of claim 5, wherein the output terminal is a drain terminal, wherein the input terminal is a source terminal, wherein the control terminal is a gate terminal, and
wherein the plurality of boot-strap switches are configured to:
when the filter bypass switch is in the OFF state, couple the at least one boot-strap capacitor to a supply voltage to charge the at least one boot-strap capacitor to the supply voltage, couple the gate terminal of the filter bypass switch to the source terminal of the bypass switch, and decouple the at least one boot-strap capacitor from 1) the gate terminal of the single bypass switch and 2) the source terminal of the single bypass switch, and
when the filter bypass switch is in the ON state, decouple the at least one boot-strap capacitor from the supply voltage, and couple the at least one boot-strap capacitor to 1) the gate terminal of the single bypass switch and 2) the source terminal of the single bypass switch to apply a combination of the supply voltage and a voltage of the input signal at the gate terminal of the single bypass switch.

7. The AFE system of claim 1, wherein the at least one sampling capacitor includes the filter capacitor.

8. The AFE system of claim 1 in combination with an electrocardiogram (ECG) measurement circuit.

9. A method of operating an analog front end (AFE) system including an anti-alias filter circuit having a filter bypass switch configured to provide at least one of a charge injection and a clock feedthrough that is independent of an input signal, the method comprising:
providing at least one sampling capacitor of an analog-to-digital converter (ADC) circuit configured to sample the output of the anti-alias filter circuit;
providing a gain or buffer circuit including an input to receive the input signal; and
coupling the anti-alias filter circuit to the output of the gain or buffer circuit, the anti-alias filter circuit including:
a filter resistor;
a filter capacitor coupled to a terminal of the filter resistor; and
the filter bypass switch connected in a boot-strapped configuration to pull a control terminal of the filter bypass switch above or below a supply voltage, the filter bypass switch connected in parallel with the filter resistor, the filter bypass switch including an ON state and an OFF state; and
wherein when in the ON state, receiving the input signal and controlling the filter bypass switch to bypass the filter resistor to allow the gain or buffer circuit to drive the at least one sampling capacitor through the filter bypass switch; and
wherein when in the OFF state, receiving the input signal and controlling the filter bypass switch to cause the gain or buffer circuit to drive the at least one sampling capacitor through the filter resistor.

10. The method of claim 9, wherein providing the anti-alias filter circuit including the filter bypass switch connected in a boot-strapped configuration includes:
providing the filter bypass switch with an input terminal configured to receive the input signal, an output terminal, and the control terminal;

providing at least one boot-strap capacitor; and
providing a plurality of boot-strap switches, the method further comprising:
when the filter bypass switch is in the OFF state, controlling the plurality of boot-strap switches to couple the at least one boot-strap capacitor to a supply voltage to charge the at least one boot-strap capacitor to the supply voltage, couple the control terminal of the bypass switch to the input terminal of the bypass switch, and decouple the at least one boot-strap capacitor from 1) the control terminal of the bypass switch and 2) the input terminal of the bypass switch, and
when the filter bypass switch is in the ON state, controlling the plurality of boot-strap switches to decouple the at least one boot-strap capacitor from the supply voltage, and couple the at least one boot-strap capacitor to 1) the control terminal of the bypass switch and 2) the input terminal of the bypass switch to apply a combination of the supply voltage and a voltage of the input signal at the control terminal of the bypass switch.

11. The method of claim 9, wherein providing the filter bypass switch includes providing a single transistor.

12. The method of claim 9, wherein providing the filter bypass switch includes providing a single type of field-effect transistor (FET) being only one of an N-type FET or a P-type FET.

13. The method of claim 12, wherein providing the filter bypass switch with an input terminal configured to receive the input signal, an output terminal, and the control terminal includes:
providing the filter bypass switch with a source terminal configured to receive the input signal, a drain terminal, and a gate terminal.

14. The method of claim 9, wherein the filter capacitor includes the at least one sampling capacitor of ADC circuit.

15. An electrocardiogram (ECG) measurement circuit comprising:
an analog front end (AFE) system including an anti-alias filter circuit having a filter bypass switch configured to provide at least one of a charge injection and a clock feedthrough that is independent of an input signal, the AFE system comprising:
at least one sampling capacitor of an analog-to-digital converter (ADC) circuit configured to sample the output of the anti-alias filter circuit;
a gain or buffer circuit including an input to receive the input signal; and
the anti-alias filter circuit coupled to the output of the gain or buffer circuit, the filter circuit including:
a filter resistor;
a filter capacitor coupled to a terminal of the filter resistor; and
the filter bypass switch connected in a boot-strapped configuration to pull a control terminal of the filter bypass switch above or below a supply voltage, the filter bypass switch connected in parallel with the filter resistor, the filter bypass switch including an ON state and an OFF state,
wherein when in the ON state, the filter bypass switch is configured to bypass the filter resistor allowing the gain or buffer circuit to drive the at least one sampling capacitor through the filter bypass switch; and
wherein when in the OFF state, the filter bypass switch is configured to cause the gain or buffer circuit to drive the at least one sampling capacitor through the filter resistor.

16. The ECG measurement circuit of claim 15, wherein the filter bypass switch connected in a boot-strapped configuration includes:
the bypass switch having an input terminal configured to receive the input signal, an output terminal, and the control terminal, and;
at least one boot-strap capacitor; and
a plurality of boot-strap switches configured to:
when the filter bypass switch is in the OFF state, couple the at least one boot-strap capacitor to a supply voltage to charge the at least one boot-strap capacitor to the supply voltage, couple the control terminal of the bypass switch to the input terminal of the bypass switch, and decouple the at least one boot-strap capacitor from 1) the control terminal of the bypass switch and 2) the input terminal of the bypass switch, and
when the filter bypass switch is in the ON state, decouple the at least one boot-strap capacitor from the supply voltage, and couple the at least one boot-strap capacitor to 1) the control terminal of the bypass switch and 2) the input terminal of the bypass switch to apply a combination voltage of the supply voltage and a voltage of the input signal at the control terminal of the bypass switch.

17. The ECG measurement circuit of claim 15, wherein the bypass switch is a single transistor.

18. The ECG measurement circuit of claim 15, wherein the bypass switch is a single type of field-effect transistor (FET) being only one of an N-type FET or a P-type FET.

19. The ECG measurement circuit of claim 18, wherein the output terminal is a drain terminal, wherein the input terminal is a source terminal, and wherein the control terminal is a gate terminal.

20. The ECG measurement circuit of claim 15, wherein the at least one sampling capacitor includes the filter capacitor.

* * * * *